United States Patent [19]

Davis

[11] 4,076,797
[45] Feb. 28, 1978

[54] RADIOIMMUNOASSAY

[75] Inventor: Raymond Vincent Davis, North Caldwell, N.J.

[73] Assignee: Hoffmann-La Roche Inc., Nutley, N.J.

[21] Appl. No.: 727,548

[22] Filed: Sep. 28, 1976

[51] Int. Cl.$^2$ .................... A61K 43/00; G01N 33/16
[52] U.S. Cl. ..................................... 424/1; 23/230 B; 424/13
[58] Field of Search ....................... 424/1, 1.5, 12, 13; 23/230 B

[56] References Cited

PUBLICATIONS

Ohta et al., Chemical Abstracts, vol. 84, No. 9, Mar. 1, 1976, p. 350, abstract No. 57311r.

Giaever, Chemical Abstracts, vol. 83, No. 17, Oct. 27, 1975, p. 362, abstract No. 145659v.

Primary Examiner—Benjamin R. Padgett
Assistant Examiner—Christine M. Nucker
Attorney, Agent, or Firm—Samuel L. Welt; Bernard S. Leon; George W. Johnston

[57] ABSTRACT

A radioimmunoassay for syphilis using *Treponema pallidum* reiter variant as the antigen in an indirect procedure is disclosed.

3 Claims, No Drawings

RADIOIMMUNOASSAY

BACKGROUND

Immunological assays for antibodies to the causative organism of syphilis (*Treponema pallidum*) in the blood of patients heretofore have been carried out by the *Treponema pallidum* Hemagglutination test (TPHA), the Fluorescent Treponema Antibody Absorption test (FTA-Abs) and the *Trepenoma pallidum* Immobilization test (TPI). These assays require a subjective estimate of antibody titer. An accurate assay in which the results are objectively determined is desirable since the results are more reproducible and can be realistically compared between different laboratories. In addition, it is desirable to have an assay in which the procedure as well as the final readout are amenable to automation.

DESCRIPTION OF THE INVENTION

This invention is based on the discovery that a radioimmunoassay for syphilis can be successfully carried out in the solid phase utilizing as the antigen, *Treponema pallidum* reiter variant (hereinafter referred to as *T. reiteri*). The assay gives reproducible, accurate, objective results despite the fact that *Treponema reiteri* is a non-infectious variant of the causative agent of syphilis, *Treponema pallidum*.

This result occurs, apparently, because the antibodies in the patient's blood are reactive with both *T. reiteri* and *T. pallidum*. However, *T. pallidum* is difficult to isolate in sufficiently pure form in such a manner that its antigenic sites are retained while *T. reiteri* can be grown *in vitro* and in small and large volume broth cultures and isolated by centrifugation while retaining its antigenic sites.

The process of this invention is an indirect radioimmunoassay. The process is a multiple step process carried out as follows.

*T. reiteri* is fixed to the bottom of appropriate test tubes. Subsequently each serum sample to be tested is diluted with FTA-Abs sorbent and 100 μl. aliquots are added to the test tubes. Then the test tubes are incubated and washed with phosphate buffered saline (PBS). A 20 μl. aliquot of appropriately radiolabelled antihuman gammaglobulin (AH γG) is added to the bottom of each test tube. The tubes are again incubated and washed with PBS. Labelled AH γG bound to antibody, which in turn has reacted with *T. reiteri*, is then measured in a gamma-scintillation counter. The percent AH γG bound indicates the amount of antibody against *T. pallidum* (or other cross-reactive treponemes) present in the serum.

The *T. reiteri* used in the radioimmunoassay of this invention is obtained from Spirolate broth culture containing 10% rabbit serum. Preferably it is grown in broth culture and washed by alternate centrifugation and resuspension in phosphate-buffered saline (PBS) prior to use. However, any source of *T. reiteri* is suitable for use in this invention. The tubes are coated on the inside bottom with *T. reiteri* by transferring an aliquot of an aqueous suspension thereof to the tube and allowing to dry. The size of the tube and concentration of *T. reiteri* are not critical to the practice of this invention as long as the proportion of antibody to antigen elicits a difference between normal and syphilitic sera. Generally, however, it is preferred to use borosilicate culture tubes which are of a size conveniently useful with scintillation counters, e.g., 12 × 75 mm. Prior to inserting the *T. reiteri* suspension in the tubes, the tubes are cleaned. Then the *T. reiteri* is fixed to the tubes by acetone or any other suitable solvent.

The amount of *T. reiteri* suspension added to each tube is not as important as the uniformity of the amount. Thus, while about 10 μl. of suspension is preferably added, care must be taken that the variation between amounts added to tubes does not vary more than 1 μl. This assures reproducible results in the assay.

The amount and dilution of the serum to be tested is chosen to assure that sufficient antibody, if any, is present to give meaningful results. The diluent, FTA-Abs sorbent, is composed of an autoclaved culture of *T. reiteri* which has been clarified by centrifugation and appropriately diluted. Various buffers and mixtures of inorganic salts, as well as protein mixtures such as normal human serum can be employed as "sorbents". The FTA-Abs sorbent, however, is preferred.

The function of the FTA-Abs sorbent is as a diluent and to bind group-specific antibodies present in patients' sera. Spirolate broth medium containing no treponemes, as well as various inorganic salt preparations have been successfully substituted for FTA-Abs sorbent. In addition, various ions which bind to hydrophobic sites, such as KSCN substitute to some degree for the sorbent in the assay of this invention.

The preferred dilution which is one part serum to 9 parts of sorbent was established on the basis of "checkerboard" experiments where various dilutions of serum were concomitantly assayed with increasing amounts of *T. reiteri*. Serum dilutions ranging from 1:2 to 1:100 are operable since such dilutions have yielded measurable differences between syphilis positive and negative sera. The antigen concentration which is determined in optical density (O.D.) units measured at 650 nm., can range from 0.05 to greater than 0.25 using 10 μl. of antigen per tube.

Suitable buffers must be within a pH range of about 6.0–8.0 preferably about pH 7.0–7.4. Typical suitable buffers are Tris-HCl and phosphate buffered saline (PBS). PBS .01M, pH 7.2 is the preferred buffer.

The radiolabelled antibody is labelled preferably with $^{125}I$, however, other radiolabels such as $^{131}I$, $^{14}C$ and $^{3}H$ could possibly be used.

In order to insure satisfactory results, the radiolabelled antibody must have sufficient specificity to enable it to react with the antigenic sites of the antibodies in the patients' serum which have reacted with *T. reiteri*.

The following Examples illustrate the inventions.

EXAMPLE 1

Preparation of Antibody 2.0 Gm. copper-treated aminocellulose are washed by alternately suspending in about 100 ml. distilled water and centrifuging at about 3,000 rpm. The washed aminocellulose is suspended in sufficient distilled water to give a total volume of 150.0 ml., which volume is cooled to 4° C. and added with 50 ml. distilled water to a mixture formed by adding 6.0 gm. NaNO$_2$ to 200 ml. of 10% HCl at 4° C. in a low actinic red 500 ml. Erlenmeyer flask and stirred 30 minutes at 4° C. The resulting slurry is filtered through Teflon filter paper on a Buchner funnel, the filter cake is washed twice with distilled H$_2$O and twice with 0.2 M sodium borate buffer, pH 8.6 at 4° C. The filter cake is added to 2 gm. of H γG dissolved in 200 ml. of borate buffer maintained at room temperature in a red 500 ml. Erlenmeyer flask and stirred for 1 hour at room temperature then overnight (about 16 hrs.) at 4° C. The resulting suspension is filtered through a fritted glass funnel (medium pore size) with suction, and washed 3 times with distilled water (about 25 ml.) and 3 times with 0.9% NaCl. With each wash, the filter cake is resuspended directly on the funnel.

The filter cake is then transferred to 200 ml. of beta-naphthol-saturated barbital buffer (5.12 gm. Na Barbital in 248 ml. $H_2O$, adjusted to pH 9.2 with about 0.5 ml. 1N HCl) at room temperature and stirred at room temperature for 1 hour, then overnight at 4° C. The resulting suspension is filtered on a fritted glass funnel (medium pore size) and washed 3 times with about 50 ml. 0.9% NaCl at 4° C.

The resulting cake is added to a slurry containing 40.0 gm of plain cellulose (Whatman CF11) in phosphate-buffered saline (pH 7.2, 0.01 M). A 2.5 × 16 cm. column is poured and equilibrated with PBS. The optical density of the effluent at 220 nm. should be <0.05 prior to addition of antiserum (AH γG).

50 Ml. of goat anti-human γglobulin is applied to the equilibrated column at room temperature and 5 ml. fractions of effluent are collected. Residual serum is rinsed onto the column with about 5 ml. of PBS and washed with the PBS until the $OD_{220nm}$ is less than 0.05. The column is transferred to a 4° C. cold room, allowed 0.5 hr. for temperature equilibration and elution with 1M NaCl, pH 3.2 at 4° C. is begun. The $OD_{220nm}$ peak is collected and dialyzed against about 10 volumes of distilled water at 4° C. The dialysate is changed twice at 2 hour intervals on the following day. Then the retentate is shell frozen and lyophilized after the final 2 hr. dialysis period. A Folin-Lowry protein analysis is performed on the product and 12.5 mg. of protein is dissolved in 1.0 ml. of 0.5 M phosphate buffer, pH 7.5.

The immunoadsorbent column described above yields approximately 50 mg. of purified AH γG, enough antibody for 360,000 tests. The same column can be used repeatedly up to 5 times. Larger immunoadsorbent columns can readily be prepared.

The purified antibody is radiolabelled by methods known in the art, with minor modifications. The Chloramine-T method of Hunter and Greenwood, Biochem. J. 91, 46 (1964) using iodine 125 is preferred.

The reaction is effected for example, by using a reaction mixture containing Chloramine T (sodium p-toluenesulfo-chloramine), purified AH γG and iodine 125 in the form of a sodium or potassium salt. The reaction takes place in about 30 minutes and is stopped by the addition of sodium metabisulfite. The function of the sodium metabisulfite is to reduce unreacted $^{125}I$ back to its salt. The radioiodinated product can be separated from residual unreacted $^{125}I$ by chromatography in a cross-linked dextran gel column, e.g., Sephadex G-25 (Pharmacia Fine Chemicals, Piscataway, N.J.).

EXAMPLE 2

T. reiteri Tubes

12 × 75 mm. borosilicate culture tubes are rinsed with acetone and allowed to air dry in an inverted position.

Using an Eppendorf micro pipette, 10 µl. of T. reiteri suspension are transferred to the bottom of acetone-washed culture tubes, with care being taken not to touch the sides of the tubes. Although the 10 µl. volumes need not be absolute, care must be taken to add uniform amounts (± 1 µl.) to each of the tubes. The tubes are allowed to dry overnight in a well ventilated hood. The cells are fixed to the glass by addition of 2 ml. of acetone, followed by incubation for 10 minutes at room temperature. The acetone is discarded and the tubes are allowed to dry in an inverted position for at least 1 hour.

EXAMPLE 3

Radioiodinating Antibody 1.5 × 25 cm. column of Sephadex G-25 is prepared using PBS-BSA as the buffer at pH 7.2, 0.01M. Prior to each use of the column 2.0 ml. of 0.1% KI, followed by 100 ml. PBS are passed through the column to flush the column. The following are added in sequence to a 2 ml. serum bottle a) 200 µl. of 0.5 M phosphate buffer, pH 7.5
b) 50 µl. of purified AH γG, 12.5 mg./ml. of protein in 0.1 M phosphate buffer, pH 7.5
c) 100 µl. (2mCi) of $Na^{125}I$ solution
d) 100 µl. chloramine T solution (120 µg./ml.).

Then incubate 30 minutes at 4° C. with periodic mixing and add 100 µl. sodium metabisulfite (10 mg./ml.) and finally mix and transfer entire reaction mixture to the washed Sephadex G-25 column using PBS-BSA buffer to transfer and to elute. 3 ml. fractions are collected with a fraction collector and 20 µl. aliquots are assayed for radioactivity.

All tubes containing the first radioactive peak off the column are pooled and diluted 1:20 with PBS-BSA buffer for use in the radioimmunoassay.

EXAMPLE 4

Radioimmunoassay

Each serum sample to be tested is diluted 1:10 v/v with sorbent and 100 µl. of each serum dilution is dispensed into the bottom of duplicate T. reiteri tubes and incubated in a moist chamber for 30 minutes.

2.0 ml. of PBS is added to each tube. The tubes are decanted and washed twice more with PBS. The tubes are decanted and inverted onto a paper towel. Excess buffer is removed from the lip and inside surface of all tubes with care being taken not to touch the antigen coat at the bottom of the tubes.

20 µl. of the $^{125}I$ AH γG prepared in Example 3 are added to the bottom of each tube. The tube is gently vortexed in order to spread the label over the entire antigen surface. The incubation and washing steps are repeated and the tube is inverted onto a paper towel after the last wash.

All tubes are counted in a gamma scintillation counter and the $^{125}I$ AH γG bound is determined by dividing the average counts obtained on each set of duplicates by the average of counts obtained for duplicate 20 µl. aliquots of the label and multiplying by 100. A comparison of T. reiteri and T. pallidum as the antigen in the assay procedure is shown in Table I wherein sensitivity is the percent true positive and specificity is the percent true negative. The FTA-Abs assay is the reference procedure. In Table I TR is non-pathogenic Trepenoma pallidum (reiter variant) and TP is pathogenic Trepenoma pallidum. Broth cultures of these microorganisms are available from the Communicable Disease Center in Atlanta, Georgia on an unrestricted basis.

Table I

| Radioimmunoassay Comparing T. reiteri with T. pallidum | |
|---|---|
| Sensitivity | Specificity |
| RIA (TR) +/FTA + = 43/48 = 90% | RIA (TR) −/FTA − = 57/60* = 95% |
| RIA (TP) +/FTA + = 22/48 = 46% | RIA (TP) −/FTA − = 47/60 = 79% |
| 19 RIA (TP)+ were RTA (TR) + | 45 RIA (TP)− were RIA (TR) − |
| Eleven FTA borderlines were all negative by RIA (TR). | |

*5 sera in a "low risk clinical group" gave exceedingly high values by RIA (TR). If these are included, specificity = 57/66 = 87%.

The results shown in Table I indicate that the RIA for syphilis, using *T. reiteri* as antigen, correlates well with FTA-Abs results. In addition, "borderline" FTA-Abs sera are generally either definitely positive or definitely negative according to the RIA of this invention.

I claim:

1. An indirect, solid phase radioimmunoassay for syphilis comprising the steps of
   (a) fixing *Treponema pallidum* reiter variant to the inner surface of a test tube,
   (b) dispensing test samples of human serum diluted with a sorbent containing group specific antibody binders into the test tube in contact with the *Treponema pallidum* reiter variant and incubating,
   (c) washing the inner surface of the test tube to remove unreacted elements of the test sample,
   (d) dispensing $^{125}$I antihuman gamma globulin into the test tube in contact with the antigenic surface and incubating,
   (e) washing the inner surface of the test tube to remove unreacted $^{125}$I antihuman gamma globulin,
   (f) measuring the radioactivity in the test tube and comparing to a standard to determine the presence or absence of syphilis.

2. The method of claim 1 wherein in step (a) the *Treponema pallidum* reiter variant is fixed to the inner surface of the test tube on and near the enclosed end thereof by adding acetone, incubating, discarding the acetone and drying.

3. The method of claim 1 wherein the antihuman gamma globulin is immunospecifically purified by immunoadsorption to human gamma globulin followed by separation therefrom prior to use.

* * * * *